US009964752B2

(12) United States Patent
Buerk

(10) Patent No.: US 9,964,752 B2
(45) Date of Patent: May 8, 2018

(54) LIGHT-CONDUCTING DEVICE FOR AN ENDOSCOPE

(75) Inventor: Andre Buerk, Villingen-Schwenningen (DE)

(73) Assignee: Karl Storz SE & Co. KG, Tuttlingen (DE)

(*) Notice: Subject to any disclaimer, the term of this patent is extended or adjusted under 35 U.S.C. 154(b) by 382 days.

(21) Appl. No.: 13/452,108

(22) Filed: Apr. 20, 2012

(65) Prior Publication Data

US 2012/0271115 A1 Oct. 25, 2012

(30) Foreign Application Priority Data

Apr. 21, 2011 (DE) ........................ 10 2011 007 878

(51) Int. Cl.

| | |
|---|---|
| ***A61B 1/06*** | (2006.01) |
| ***G02B 6/06*** | (2006.01) |
| ***G02B 23/24*** | (2006.01) |
| ***A61B 1/07*** | (2006.01) |
| ***F21V 8/00*** | (2006.01) |
| ***A61B 1/00*** | (2006.01) |
| *G02B 6/04* | (2006.01) |

(52) U.S. Cl.

CPC ........ *G02B 23/2469* (2013.01); *A61B 1/0011* (2013.01); *A61B 1/07* (2013.01); *G02B 6/0006* (2013.01); *G02B 6/04* (2013.01); *Y10T 29/49826* (2015.01)

(58) Field of Classification Search

CPC .... A61B 1/00167; G02B 6/4255; G02B 6/04; G02B 6/403

USPC ........ 600/182; 362/554, 556, 574, 572–573; 385/117

See application file for complete search history.

(56) References Cited

U.S. PATENT DOCUMENTS 2,855,322 A * 10/1958 Field ........................ C08L 1/10 106/170.45
3,269,387 A * 8/1966 Wallace ........................ 600/153
3,681,164 A * 8/1972 Bazinet ................... C03B 37/15 156/180

(Continued)

FOREIGN PATENT DOCUMENTS

DE 1207115 B 12/1965
DE 10344169 A1 5/2005

(Continued)

OTHER PUBLICATIONS

German Search Report; Application No. DE 10 2011 007 878.9; dated Feb. 1, 2012; 5 pages.

*Primary Examiner* — Matthew J Kasztejna
*Assistant Examiner* — Rynae Boler
(74) *Attorney, Agent, or Firm* — Whitmyer IP Group LLC

(57) ABSTRACT

A light-conducting device for an endoscope for conducting observation light from a proximal end of the endoscope to a distal end of the endoscope includes a number of optical fibers. Each optical fiber includes a proximal end with a light inlet surface, which is provided for positioning on a proximal end of an endoscope, and a distal end with a light outlet surface, which is provided for positioning on a distal end of an endoscope. Each of the number of optical fibers including in a proximal region a first cross-section with a first surface area, and in a distal region a second cross-section with a second surface area. The first surface area is larger than the second surface area.

14 Claims, 2 Drawing Sheets

(56) References Cited

U.S. PATENT DOCUMENTS 4,483,585 A * 11/1984 Takami .................... A61B 1/07 385/115
4,544,231 A * 10/1985 Peterson ................ G02B 6/241 385/71
4,710,216 A * 12/1987 Harada ................. C03B 37/023 65/31
4,934,340 A * 6/1990 Ebling ................. A61B 1/0058 600/117
5,058,985 A * 10/1991 Davenport ............. G02B 6/403 362/558
5,160,565 A * 11/1992 Chazalon et al. ............ 156/242
5,172,685 A * 12/1992 Nudelman .................... 600/108
5,371,826 A 12/1994 Friedman
5,599,278 A * 2/1997 Hibbard ............. A61B 1/00142 600/133
5,733,029 A * 3/1998 Monroe ............... G02B 6/4248 362/109
5,941,817 A * 8/1999 Crawford ........... A61B 1/00071 600/109
6,556,851 B1 * 4/2003 Ott et al. ...................... 600/310
2003/0138753 A1 7/2003 Galarza
2003/0202760 A1 * 10/2003 Henze .................... G02B 6/403 385/115
2006/0270907 A1 * 11/2006 Klemm .................... A61B 1/07 600/177
2007/0019916 A1 * 1/2007 Takami .............. A61B 1/00167 385/117
2007/0088201 A1 * 4/2007 Eisenkolb ............ A61B 1/0011 600/182
2007/0092188 A1 * 4/2007 Hoefig ................. A61B 1/0011 385/117
2009/0116260 A1 5/2009 Rovegno
2009/0312609 A1 * 12/2009 Shimotsu ................. A61B 1/07 600/182
2011/0313243 A1 * 12/2011 Zubiate et al. ............... 600/104

FOREIGN PATENT DOCUMENTS

JP 01185509 A * 7/1989
WO 0005609 A1 2/2000

* cited by examiner

A-A

B-B

LIGHT-CONDUCTING DEVICE FOR AN ENDOSCOPE

CROSS-REFERENCE TO RELATED APPLICATIONS

The present application claims priority of German patent application No. 10 2011 007 878.9 filed on Apr. 21, 2012, the content of which is incorporated herein by reference.

FIELD OF THE INVENTION

The present invention relates to a light-conducting device for an endoscope for conducting illuminating light from a proximal end to a distal end of the endoscope.

BACKGROUND OF THE INVENTION

In medical and technical endoscopy, as a rule it is necessary to illuminate the object under observation. To generate illuminating light with a high light beam and desired spectral properties, in particular good color reproduction, use is often made of separate light source devices with high-pressure gas discharge lamps, halogen bulbs or other light sources. The light source device is connected with the proximal end of the endoscope by means of a flexible light-conducting cable. The illuminating light is transmitted from the proximal end to the distal end of the endoscope by means of one or more bundles of light-conducting fibers.

Considerable effort is required in constructing and manufacturing endoscopes for precise arrangement of the light-conducting fibers, in particular their proximal and distal ends. A further difficulty in construction and manufacture is the fact that, between the light-conducting cable and the light outlet surfaces on the distal end of the endoscope, the divergence or angular distribution of the illuminating light needs to be adjusted to the visual field (in the sense of a solid angle) that is to be illuminated. Often used here is a so-called fiber cone, which is produced as a separate component and mounted on the proximal end of the endoscope. A fiber cone includes a short bundle of light-conducting fibers whose cross-sections change from the light inlet surface to the light outlet surface, in particular becoming smaller. The light outlet surface of the fiber cone and the light inlet surface of the bundle of light-conducting fibers must be combined with one another in such a way that a low-loss optical coupling is durably ensured.

There is a clear tendency to produce constantly thinner endoscope shafts. Conventional concepts are reaching their limits in terms of increasing miniaturization, but have proved themselves in wide applications over time and have been considerably optimized. It is therefore especially difficult to predict, in the case of endoscopes, which aspects of conventional concepts can be further developed and exploited and which aspects lend themselves to fundamental new departures. The present invention focuses on selected aspects of the illuminating beam path.

SUMMARY OF THE INVENTION

It is an object of the present invention to provide an improved light-conducting device to conduct illuminating light from a proximal end to a distal end of an endoscope, as well as an improved endoscope.

This task is fulfilled through the contents of the independent claims.

Refinements are indicated in the dependent claims.

Embodiments of the present invention are based on the idea of providing a pre-fabricated and comprehensive light-conducting device, which even before incorporation in an endoscope, comprises all properties and characteristics required for conducting illuminating light from an output to be coupled with the proximal end of the endoscope to the distal end of the endoscope. As a result, the endoscope can be manufactured more cost-effectively and with greater precision. In addition, a light-conducting device as described here can simplify further miniaturization, in particular further reduction of the cross-section of the shaft.

A light-conducting device for an endoscope, to conduct illuminating light from a proximal end of the endoscope to a distal end of the endoscope, includes a number of optic fibers, such that each light fiber comprises a proximal end with a light inlet surface that is provided for an array at a proximal end of an endoscope, and a distal end with a light outlet surface that is foreseen for an array at a distal end of an endoscope, such that the optic fibers each comprise a first cross-section with a first surface area in a proximal region and a second cross-section with a second surface area in a distal region, and such that the first surface area is greater than the second surface area.

A light-conducting device with the described properties and characteristics can be substantially or completely pre-fabricated before insertion in the endoscope and thereby can include the entire illuminating beam path to conduct or transmit illuminating light inside the endoscope. Consequently the manufacture of the entire endoscope can be simplified. As a result, manufacture of the light-conducting device and production of other components of the endoscope can occur separately in terms of space and time, as well as with considerable logistical independence of one another.

The light-conducting device, especially with the characteristics described below, can be mechanically robust in configuration, in particular because the optic fibers remain constant, as a single unit, from the proximal to the distal end. In particular, a separate fiber cone is not required in the light-conducting device. This can accomplish more than just simplifying the production of the light-conducting device and/or of the endoscope. Because of the absence of a border surface between a light outlet surface of a fiber cone and a light inlet surface of a bundle of optic fibers, the mechanical robustness and optical degree of effectiveness can be improved and/or losses of illuminating light at this border surface can be avoided. Because losses of illuminating light as a rule are accompanied by corresponding thermal impact, the thermal impact of the light-conducting device described here can be lesser. This can simplify the design of the light-conducting device and of the entire endoscope and increase their useful life.

The light-conducting device is configured especially for an endoscope for a medical application and/or for an endoscope for a technical or non-medical use. Optic fibers, of the number of optic fibers, especially at or close to their distal ends, can be combined into several bundles that are to be positioned at various sites on the distal end of an endoscope, and/or that are provided to transmit illuminating light that is to be radiated in various solid angle fields. Here the proximal ends of the optic fibers of the number of optic fibers are particularly combined into a single bundle. In other words, the optic fibers of the number of optic fibers can be combined at their proximal ends into a bundle that, downstream in the light path or in the direction of the distal end, breaks down or is divided into several bundles. In this configuration the light-conducting device is therefore also suited, for example, for an endoscope on whose distal end illuminating light emerges via several light outlet surfaces into a large solid angle field.

The light inlet surface of the number of optic fibers, in particular, directly form an optical interface to a fiber optic cable or are intended and configured for direct optical coupling with a light outlet surface of a fiber optic cable by which the endoscope can be connected with a light source device. The number of border surfaces on which illuminating light can be reflected, dispersed or absorbed can thereby be minimized. This can contribute toward improving the optical effectiveness, reducing losses of illuminating light, and reducing thermal impact along the illuminating beam path.

The proximal region, in which an optical fiber comprises a first cross-section with a large surface area, borders in particular on the light inlet surface. The distal region, in which an optical fiber comprises a second cross-section with a small surface area, borders in particular on the light outlet surface. The distal region is, in particular, substantially longer than the proximal region.

Already conditioned by the processes used in their production, the cross-sections of the optical fibers, both in the proximal and distal regions and in other regions situated between the proximal and distal regions, can have a certain dispersal, but in such a way that the overwhelming majority of the optical fibers comprise cross-sections that have a greater surface area in the proximal than in the distal region.

In a light-conducting device as described here, the surface area of the cross-section of an optical fiber can constantly decrease in the downstream direction in the light path, in a transition area between the proximal and distal regions.

Because of the aforementioned possible dispersal in production processes, individual optical fibers (especially in undesired manner) can comprise different cross-sections from the overwhelming majority of optical fibers. Statements applying to optical fibers of the number of optical fibers are therefore to be understood in particular in such a way that the comment is valid for the clear majority of optical fibers.

The transitional area extends, in particular, from the distal end of the proximal region, or the downstream end in the light path, to the proximal end, upstream in the light path, of the distal region. Alternatively an additional region is situated, for example, between the proximal region and the transitional area, so that the cross-section of an optical fiber in this additional region can be distinguished from the cross-section of the optical fiber in the proximal region, but in particular so that the surface areas of the cross-section in the additional region and of the cross-section in the proximal region are equal or essentially equal.

The cross-sections of the optical fibers in the proximal region and in the distal region are selected, in particular, in such a way that the total cross-section of the number of optical fibers at their proximal ends or the light inlet surface is adapted to the cross-section of a light-conducting cable that is to be used to transmit illuminating light from a light source device to the endoscope, and in such a way that illuminating light emerges at the light outlet surfaces of the optical fibers with a desired divergence or with a desired angular distribution or in a desired solid angle field. The latter depends primarily on the divergence or angular distribution of the illuminating light switched into the light inlet surface—and thus on properties of the light source device and of the light-conducting cable that are to be used—as well as on the ratio of the cross-sections and especially of the surface areas of the cross-sections of the optical fibers at their light inlet surfaces and at their light outlet surfaces. Therefore, by modifying the cross-section of an optical fiber in the transitional area, the divergence or angular distribution of the illuminating light emerging at the light outlet surface can be adjusted.

With a light-conducting device with a transitional area, as described here, the optical fibers in the transitional area, in particular, are positioned in the same or essentially the same direction or orientation in which they are positioned in the proximal region.

In particular, the optical fibers, at least in the proximal region, in the transitional area, possibly in the aforementioned additional region between the proximal region and the transitional area, and optionally in an additional region that adjoins the transitional area downstream in the light path, are straight or essentially straight. The proximal regions and the transitional areas of the optical fibers of the light-conducting device are, in particular, provided for positioning in the region of a coupling on the proximal end of an endoscope, and the coupling is provided for optical and mechanical coupling of the endoscope with a light-conducting cable. The coupling can be positioned perpendicular or essentially perpendicular, or at a 45-degree angle, or at another angle, to the longitudinal axis of a shaft of the endoscope.

A light-conducting device with a transitional area, as described here, further includes a framing sheath, such that the proximal regions and the transitional areas of the number of optical fibers are positioned inside the framing sheath.

The framing sheath is especially configured to enclose and mechanically to stabilize the proximal regions and the transitional areas of the optical fibers and to provide the proximal end, or the end downstream in the light path, of the light-conducting device with a defined geometric shape and sufficient mechanical robustness. The framing sheath, in particular, has the shape of a cylindrical mantle with circular, elliptical, rectilinear or other polygonal cross-section, or of a conical or pyramid-shaped stump with circular, elliptical, rectilinear or generally polygonal base surface.

In manufacturing an endoscope, the framing sheath can be joined in the aforementioned coupling area on the proximal end of the endoscope. In particular, the framing sheath is configured to constitute in itself a coupling or part of a coupling of an endoscope for coupling with a light-conducting cable.

In particular with a framing sheath, the light-conducting device can comprise advantageous mechanical properties and thus also advantageous properties concerning manufacture of an endoscope—the framing sheath holds and protects the proximal regions and the transitional areas of the optical fibers—on the downstream end of the framing sheath in the light path, the optical fibers emerge already with the small second cross-sections of the distal region and thus can be handled flexibly and easily.

With a light-conducting device with a framing sheath, as described here, the framing sheath in particular includes a material whose thermal expansion coefficient differs from the thermal expansion coefficients of optical fibers by no more than $2*10^{-6}\ K^{-1}$.

Mechanical tensions between the framing sheath and the optical fibers occurring from temperature modifications can be prevented or largely reduced with a small difference in the thermal expansion coefficients of the materials of the framing sheath on the one hand and of the optical fibers on the other hand. The light-conducting device can thus also withstand without damage even repeated heating to high temperatures such as prevail in autoclaving an endoscope.

With a light-conducting device with a framing sheath, as described here, the framing sheath is particularly configured and provided to be positioned at least partly inside a region of a coupling for optical coupling of the endoscope with a light-conducting cable.

Arranging a framing sheath at least partly inside the region of the coupling can make possible a compact structure of an endoscope with the light-conducting device.

Alternatively, the transitional areas of the optical fibers are provided and configured to be positioned at a distance from a coupling of an endoscope, with or without a framing sheath surrounding and mechanically protecting them. In particular, the transitional areas can be configured at a distance from the coupling for positioning in the shaft of an endoscope or in a component of the endoscope that connects proximally on the shaft.

A light-conducting device as described here can also include a first casting compound that is positioned between the transitional areas of the optical fibers.

The first casting compound comprises, in particular, a cement, a thermoplastic or duroplastic synthetic material or other organic or inorganic material. The elasticity of the first casting compound is adjusted, in particular, to the elasticity of the material of the optical fibers in order to mechanically support the transitional areas of the optical fibers. For this reason, the first casting compound, in particular, is positioned in an area, or fills the intervals between the optical fibers in an area, that includes the entire transitional areas of the optical fibers. The area in which the casting compound is positioned can, in addition, include regions of the optical fibers that adjoin the transitional areas upstream and/or downstream in the light path.

Providing the first casting compound between the transitional areas of the optical fibers can markedly increase mechanical robustness of the light-conducting device, especially since in fact the transitional areas of the optical fibers can be highly brittle in the absence of protection.

A light-conducting device with a first casting compound between the transitional areas of the optical fibers can, in addition, comprise a second casting compound that is positioned between the optical fibers and that has a higher elasticity than the first casting compound, so that the second casting compound is positioned downstream in the light path from the first casting compound.

The second casting compound encases, in particular, proximal portions of the distal region of the optical fibers, in which the latter have the second, smaller cross-section. The second casting compound, in particular, borders directly on the first casting compound or fills a spatial area that borders directly on the spatial area filled by the first casting compound. The second casting compound with its higher elasticity can provide a soft or essentially continuous transition between the essentially rigid framing of the optical fibers by the first casting compound and the free and elastic individual fibers. The local mechanical voltage spikes, which are generated by forces acting on the distal regions of the optical fibers, can thereby be markedly reduced. Thus, because of the second casting compound, it is possible to increase the mechanical robustness of the light-conducting device and the service life of the light-conducting device and of an endoscope that is provided with the light-conducting device and is exposed to numerous autoclaving processes, especially during its service life.

The first casting compound, and possibly also the second casting compound, are, in particular, positioned inside the framing sheath described above.

With a light-conducting device as described here, the optic fibers of the number of optic fibers, in particular in the proximal region, can be at least either soldered or melted or welded or cemented or cast together.

The proximal areas of the optical fibers that are fused together can form a rigid and robust unit. In addition, the optical fibers can be fused with one another fluid-tight so that, in particular, the light inlet surfaces of the optic fibers can directly form a surface of an endoscope through which no moisture can penetrate even during an autoclaving process.

With a light-conducting device in which the optical fibers in the proximal region are fused together, the optical fibers can include cross-sections in their proximal regions that depart from circular shape.

In particular, because of a mechanical pressure exerted during the manufacture of the light-conducting device within a plane perpendicular to the longitudinal axes of the optical fibers, the cross-sections of the optical fibers in their proximal regions have cross-sections that depart from circular shape, for example hexagonal, essentially hexagonal or other polygonal cross-sections. To generate these cross-sections, the optical fibers have a temperature during the exerting of the aforementioned pressure that is, in particular, close to their glass transition temperature or deformation temperature. The described reforming of the optical fibers with otherwise especially circular cross-sections makes possible a reduction or removal of intervals. The aforementioned fluid-tight insulation can thereby be obtained. In addition, the degree of effectiveness of the switching of illuminating light at the light inlet surfaces to the optical fibers can be increased because the portion of the illuminating light switched into intervals instead of into optical fibers can be markedly reduced.

With a light-conducting device as described here, the distal ends of optical fibers of the number of optical fibers can be at least either soldered or welded or cemented or cast together.

In particular, the distal ends of bundles out of a partial number of the number of optical fibers are joined together in one of the ways described. Optionally, in addition, a sheath can be provided that encloses the joined distal ends in mantle shape. The distal ends of the optical fibers are, in particular, fused in fluid-tight manner in order to prevent penetration of fluid into an endoscope manufactured with the light-conducting device, even during an autoclaving process. The fused distal ends of the optical fibers can be processed in such a way that after insertion into one or (in the event of several bundles) more corresponding openings on the distal end of an endoscope, they need no further processing. In particular, by polishing the fused ends of the optical fibers, the light outlet surfaces of the optical fibers are positioned in a smooth surface, in particular in a plane.

This extensive prefabrication of the light-conducting device, even including the distal ends and light outlet surfaces of the optical fibers, can simplify manufacture of an endoscope with the light-conducting device and, in particular, can support a temporal, spatial and logistical separation of manufacturing steps that also include the illuminating beam path, from other manufacturing steps for an endoscope.

An endoscope includes a light-conducting device as described here. The described advantages of embodiments of the light-conducting device lead to corresponding advantages of the endoscope, in particular the possibility of a farther-reaching miniaturization and/or a reduction of manufacturing costs.

The endoscope, as already indicated above, can comprise a coupling for optical coupling of the endoscope with a separate light source via a light-conducting cable. Alternatively, the endoscope can comprise an integrated light source on the proximal end. In this case the light inlet surface is, in particular, positioned in the endoscope in such a way as to switch light from the light source—if necessary, after collimation or bundling by means of a mirror and/or one or more lenses—directly into the light inlet surface.

With a method to produce an endoscope, a light-conducting device as described here and a sub-assembly for an endoscope are provided and the light-conducting device is inserted into the sub-assembly in order to produce the endoscope.

The light-conducting device comprises in particular, even before insertion into the sub-assembly, all optical functions of the illuminating beam path of the endoscope that is to be produced. The light-conducting device and the sub-assembly can be produced at different locations and at different times, so that the entire production process can be optimized and executed more economically.

BRIEF DESCRIPTION OF THE DRAWINGS

Embodiments are explained in further detail below with reference to the appended drawings, which are as follows.

DETAILED DESCRIPTION OF THE INVENTION

Figure 1:
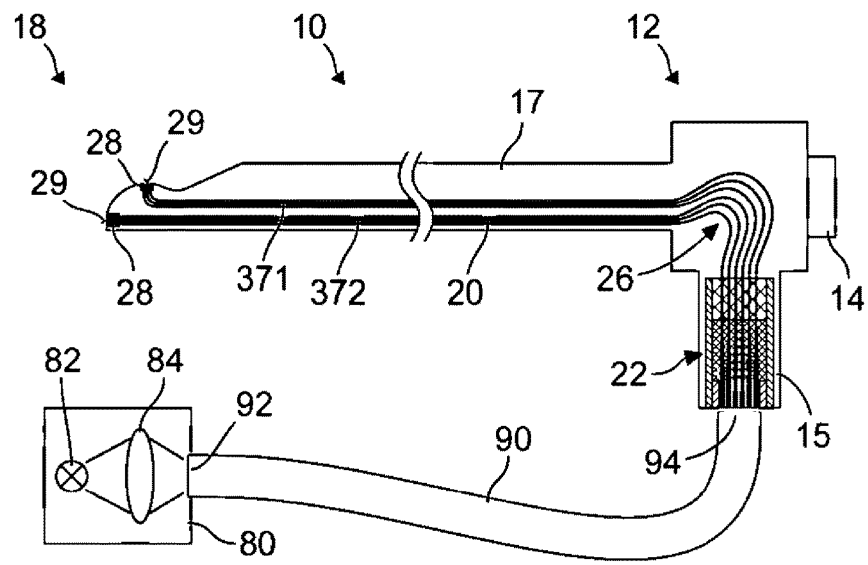
FIG. 1 shows a schematic depiction of an endoscope.

FIG. 1 shows a schematic depiction of an endoscope 10, a light source device 80 and a light-conducting cable 90 that optically couples the light source device 80 with the endoscope 10. The endoscope 10 comprises a proximal end 12 and a distal end 18. A shaft 17 of the endoscope 10 extends from the proximal end 12 to the distal end 18 of the endoscope 10. The shaft 17 in each case can be, either in sections or completely, rigidly straight, rigidly curved or flexible. No further detail is provided hereinafter on the observation beam path and/or the positioning and configuration of a light-sensitive image sensor on the proximal end 12 or on the distal end 18 of the endoscope 10. An eyepiece 14 is indicated by way of example on the proximal end 12 of the endoscope 10.

On the proximal end 12 the endoscope 10 comprises a coupling 15 for the light-conducting cable 90. The coupling 15 is, in particular, oriented in a direction perpendicular or essentially perpendicular to the longitudinal axis of the shaft 17. Departing from the depiction in FIG. 1, the coupling 15 can have a different orientation, for example being positioned at an angle of 45 degrees to the longitudinal axis of the shaft 17. Positioned in the endoscope 10 is a light-conducting device 20 for illuminating light, which extends from the proximal end 12 to the distal end 18 of the endoscope 10.

A proximal end 22 of the light-conducting device 20 is positioned in the area or at least partly in the area of the coupling 15. Contrary to the depiction in FIG. 1, the proximal end 22 of the light-conducting device 20 can itself be configured to form the coupling 15 of a part of the coupling 15.

Downstream in the light path from the proximal end 22, the light-conducting device 20 comprises a curved portion 26, in which the direction of individual fibers and the light propagation direction of illuminating light inside the light-conducting device 20 changes as a result by about 90 degrees in the illustrated example. The curved portion 26 of the light-conducting device 20 allows a longitudinal compensation, which can be necessary in autoclaving the endoscope 10, for example because of the different thermal expansion coefficients of the light-conducting device 20 and the shaft 17 of the endoscope 10.

Downstream in the light path from the curved portion 26, the light-conducting device 20 extends in one or—as indicated in FIG. 1—in several partial strands along the shaft 17 to the distal end 18 of the endoscope 10. As already indicated in FIG. 1 and explained hereinafter with reference to FIGS. 2 through 4, the light-conducting device 20 comprises a number of optic fibers that are positioned in several bundles or strands 371, 372, at least at the distal end 18 and in particular also in the shaft 17 of the endoscope 10.

On the distal end 18 of the endoscope 10, the light-conducting device 20 comprises one or—as indicated in FIG. 1—several distal ends 28, each with one light outlet surface 29. In the example indicated in FIG. 1, the light outlet surfaces 29 have different orientations in order to be able to irradiate illuminating light corresponding to various adjustable viewing directions of the endoscope 10 simultaneously or alternatingly in different observation directions.

The light source device 80 includes, in particular, a light source 82 and a convergent lens 84. The light source 82 includes, for example, a high-pressure gas discharge lamp, a halogen light bulb, a light-emitting diode or a laser. The convergent lens 84 is positioned and configured to switch observation light generated from the light source 82 into a first end 92 of the light-conducting cable 90 that is connected with the light source device 80 and whose second end 94 is coupled with the coupling 15 of the endoscope 10.

Figure 2:
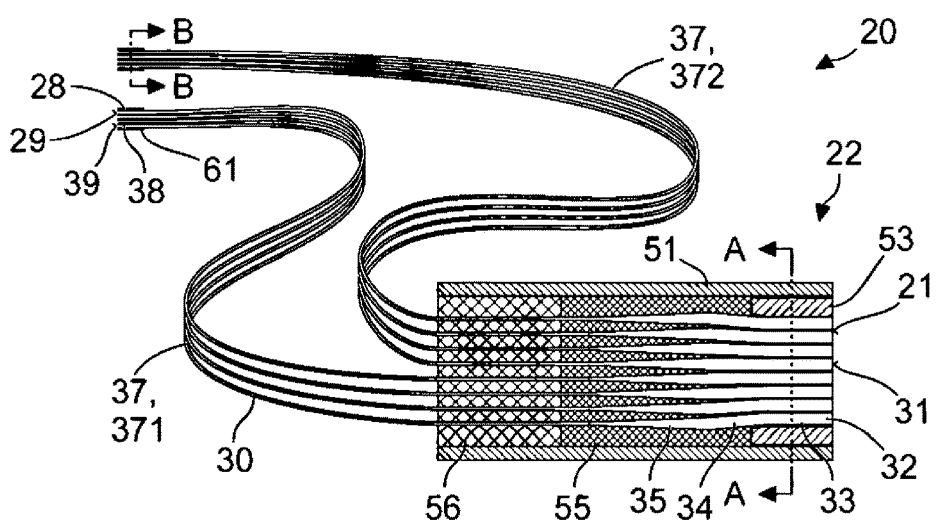
FIG. 2 shows a schematic depiction of a light-conducting device.

FIG. 2 shows a schematic depiction of the light-conducting device 20 from FIG. 1. The schematic depiction in FIG. 2 has the character of a sectional depiction, especially on the proximal end 22, while the sectional plane is parallel to the plane of projection of FIG. 1. Sections indicated in FIG. 2 along the planes A-A and B-B perpendicular to the plane of projection of FIG. 2 are described below with reference to FIGS. 3 and 4.

The light-conducting device 20 includes a number of optical fibers 30. The number of optical fibers of a real light-conducting device according to the present invention, as well as the lengths, diameters and other dimensions, can markedly differ from the schematic depictions in FIGS. 1 through 4.

Every optical fiber 30 comprises a proximal end 32 with a light inlet surface 31 and a distal end 38 with a light outlet surface 39. Between the light inlet surface 31 or the proximal end 32 on the one hand and the distal end 38 or light outlet surface 39, every optical fiber 30 comprises a framing area 33, a transitional area 35 and a flexible area 37. The flexible area 37 is also referred to as the distal region. The framing area 33 adjoins immediately with the light inlet surface 31 and includes the proximal end 32. Between the framing area 33 and the transitional area 35 there is an intermediate area 34.

An optical fiber 30 comprises in the framing area 33 and in the intermediate area 34, in particular, various cross-sections with essentially equal surface areas. The surface areas of the cross-sections of an optical fiber 30 in the framing area 33 and in the intermediate area 34 are larger or substantially larger than the surface area of the cross-section of the optical fiber 30 in the flexible area 37. In the transitional area 35, the cross-section of an optical fiber 30 continually varies from the larger cross-section in the intermediate area 34 to the smaller cross-section in the flexible or distal region 37.

Contrary to the depiction in FIG. 2, the optical fibers 30 comprise no sharp bends or corners, in particular on the borders between the framing area 33 and the intermediate area 34 and between the intermediate area 34 and the transitional area 35. The bends recognizable in the schematic depiction in FIG. 2 merely indicate that the packing density of the optical fibers 30 in the framing area 33 and in the intermediate area 34 can be of different heights. In particular, the framing areas 33 of the optical fibers 30—as described hereinafter—can be packed very thickly, while the intermediate areas of the optical fibers are packed less thickly.

The framing area 33 of the optical fibers 30 are surrounded by a pressure ring 53 in a plane perpendicular to the plane of projection of FIG. 2 and parallel to the sectional plane A-A. The framing areas 33, the intermediate areas 34, the transitional area 35 and one part each of the flexible or distal areas 37 of the optical fibers are positioned together with the pressure ring 53 in a framing sheath 51.

The framing sheath 51 and the pressure ring 53 are each, in particular, of tubular shape or have the shape of a mantle of a cylinder with circular, elliptical or polygonal cross-section. Contrary to the depiction in FIG. 2, both the framing sheath 51 and the pressure ring 53 can each have a non-cylindrically symmetrical shape. In particular, the framing sheath 51 can comprise an outer thread, a bayonet coupling device or other devices for detachable mechanical coupling of an endoscope, into which the light-conducting device 20 is inserted, with a light-conducting cable 90 (compare FIG. 1). In addition, the framing sheath 51 can be conical, tapered or pyramidal in shape with a circular, elliptical, polygonal or other cross-section.

The framing sheath 51 further includes a first casting compound 55 and a second casting compound 56. The first casting compound 55 surrounds the intermediate areas 34 and the transitional areas 35 as well as optionally short portions of the distal or flexible areas 37 of the optical fibers that adjoin with transitional areas 35 downstream in the light path and fills their intermediate spaces largely or completely. The second casting compound 56 is positioned in an area inside the framing sheath 51 that adjoins with the area downstream in the light path that is filled by the first casting compound 55.

Both the first casting compound 55 and the second casting compound 56 comprise, for example, a cement, an elastomer or other thermo-plastic or duro-plastic synthetic material. The first casting compound 55 comprises a low elasticity and causes primarily a mechanical fixing and stabilizing of the transitional areas 35 of the optical fibers 30, which can have an especially high mechanical sensitivity, especially being particularly fragile or brittle. The second casting compound 56 has a substantially higher elasticity in order to avoid local mechanical voltage spikes with forces acting on the optical fibers 30 and thus to reduce the risk of breaking individual optical fibers 30.

The distal portions 37 of the optical fibers 30 are for the most part situated outside the framing sheath 51. The lengths of the distal regions 37 of the optical fibers 30 are essentially determined by the length of the shaft 17 of the endoscope 10 for which the light-conducting device 20 is provided. The optical fibers 30 have distal regions 37 with small cross-sections with diameters ranging typically from a few micrometers to a few tens of micrometers. The optical fibers 30 therefore have distal regions 37 with high elasticity that also allows small radii of curvature in a range from a few to several millimeters even when the optical fibers 30 are of glass or a similarly brittle material.

The distal regions 37 of the optical fibers 30 positioned in one or—as indicated in FIG. 2—two or more bundles 371, 372. Both the number of bundles 371, 372 and the number of optical fibers per bundle 371, 372 and the positioning of the optical fibers 30 within the bundles 371, 372 can in fact depart strongly from the schematic depiction in FIG. 2. It can be advantageous for an endoscope with an adjustable observation direction to have six, eight, ten or more bundles 371, 372 to transmit illuminating light that is to irradiate on the distal end 18 of the endoscope 10 in different illuminating directions. A bundle 371, 372 can include several tens or several hundreds of optical fibers 30, which are not required to be positioned alongside one another in the shape of a band as indicated in FIG. 2.

The distal ends 28 of the light-conducting device 20 are formed by the distal ends 38 of the optical fibers 30. The distal ends 38 of the optical fibers 30 of a bundle 371, 372 are each enclosed by a framing sheath 61 and continuously mechanically held together. Instead of the framing sheath 61 or in addition, the distal ends 38 of the optical fibers 30 of a bundle 371, 372 can be soldered, melted, welded, cemented or cast together. As a result, the distal ends 28 of the light-conducting device 20 are rigid within a short length of, for example, just a few hundred micrometers or one or more millimeters. This can simplify handling of the distal ends 28 of the light-conducting device 20, in particular on inserting the distal ends 28 into corresponding openings on the distal end 18 of an endoscope.

The light outlet surfaces 39 on the distal ends 38 of the optical fibers 30 of a bundle 371, 372 together constitute one light outlet surface 29. In particular, after the fusing of the future distal ends 38 of the optical fibers 30 as described above, the optical fibers are cut to length and the front surfaces are polished in order to generate the light outlet surfaces 39 of the individual optical fibers in a plane and thus the light outlet surfaces 29 of the light-conducting device 20 in the desired optical quality.

The described processing and generating of the light outlet surface 29 can occur even before the light-conducting device 20 is inserted into an endoscope 10, so that after inserting the light-conducting device 20 into the endoscope 10, no additional processing steps are required on the light-conducting device 20 and thus on the illuminating beam path of the endoscope.

Figure 3:
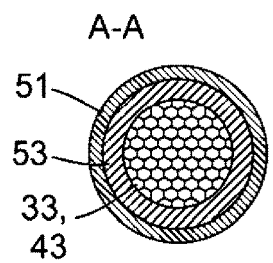
FIG. 3 shows a schematic depiction of a first cross-section of the light-conducting device from FIG. 2.

FIG. 3 shows a schematic depiction of a section along the plane A-A indicated in FIG. 2, perpendicular to the longitudinal axes of the optical fibers 30 in their framing areas 33. The framing areas 33 of the optical fibers 30 of the light-conducting device 20 are held together by the essentially annular-shaped pressure ring 53. The pressure ring 53 is surrounded by the framing sheath 51 in mantle shape.

Contrary to the depiction in FIG. 2, the coupling 15 can comprise a collar protruding radially inward, which in particular extends as far as the border of the light inlet surface 21 or of the pressure ring 53 or adjoins in each case with it. Thus the framing sheath 51 and in some cases the pressure ring 53 would be covered up. This collar covers the front end of the framing sheath 51 and in some cases of the pressure ring 53. Owing to the collar, the framing sheath 51 and in some cases the pressure ring 53 can be protected from environmental impact, for example in cleaning and sterilization of the endoscope 10. The framing sheath 51 or pressure ring 53 in this case can include a material that is not required to meet very high or even any requirements with respect to biocompatibility and corrosion resistance.

The cross-sections 43 of the framing areas 33 of all or almost all optical fibers 30 are polygonal or essentially polygonal and are contiguous with one another, in particular without gaps. Before framing the framing areas by the pressure ring 53, the framing areas 33 also each have, in particular, circular or essentially circular cross-sections. By heating to a temperature in the range of the glass transition of the material of the optical fibers and by simultaneous exertion of pressure within the plane A-A, the cross-sections 43 of the framing areas 33 of the optical fibers are reshaped, while the surface areas of the cross-sections, in particular, remain unchanged or essentially unchanged if no length modification, or essentially no length modification, of the optical fibers is caused in their framing areas 33. Here in the ideal case the hexagonal or essentially hexagonal cross-sections 43 shown in FIG. 3 emerge in the positioning of a hexagonal two-dimensional grid.

The configuration of the framing areas 33 of the optical fibers 30 described with reference to FIG. 3 minimizes or eliminates intervals between the framing areas 33 of the optical fibers 30. This can improve the effectiveness of the switching of illuminating light to the light inlet surface 21 of the light-conducting device 20, because a smaller portion of the illuminating light is switched into intervals between optical fibers and becomes lost there. In addition, the framing areas 33 reshaped in the described manner by heat and pressure can form a fluid-tight body. The light inlet surface 21 of the light-conducting device 20, from the light inlet surfaces 31 of the optical fibers 30, can thus directly form an outer surface of an endoscope 10 that is not to be further insulated and by which no gas and no liquid can penetrate the interior of the endoscope 10 even during an autoclaving process.

Alternatively to the reshaping and melting of the framing areas 33 of the optical fibers 30 by heat and pressure, as described with reference to FIG. 3, the framing areas 33 of the optical fibers 30—depending, among other things, on the material of the optical fibers 30—can be joined, in particular soldered, welded, cemented or cast by other means. Even in this way it is possible to generate fluid-tight insulation under some circumstances.

Figure 4:
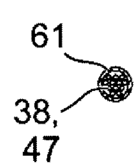
FIG. 4 shows a schematic depiction of a second cross-section of the light-conducting device from FIG. 2.

FIG. 4 shows a schematic depiction of a section along the plane B-B, indicated in FIG. 2, perpendicular to the longitudinal axes of the distal ends 38 of the optical fibers 30 of a bundle 371, 372. The distal ends 38 of the optical fibers 30 are, in particular, framed in the framing sheath 61 already indicated in FIG. 2. Alternatively or in addition, the distal ends 38 of the optical fibers 30 can be welded, melted, soldered, cemented or cast together. By means of a cement, casting compound or solder between the distal ends 38 of the optical fibers 30, a fluid-tight body can be formed that can be suitable for preventing penetration of a fluid into an endoscope. Departing from the depiction in FIG. 4, the cross-sections of the distal ends 38 of the optical fibers 30 can have non-circular cross-sections, for example caused by reshaping by heat and pressure as is described above with reference to FIG. 3.

Before joining, both the framing areas 33 and the distal ends 38 of the optical fibers 30 can be compressed, in particular, by a pressure device in the plane A-A or B-B. As a result of the compression, a heightened packing density develops, in particular by a hexagonal or essentially hexagonal arrangement of the framing areas 33 or of the distal ends 38 of the optical fibers 30, as is indicated with reference to FIG. 3 or 4. The compression can be supported by use of a gliding agent, by ultrasound or other measures that reduce friction between framing areas 33 or between the distal ends 38 of the optical fibers 30.

It is possible to save construction space by means of the cross-sections of the distal ends 38 of the optical fibers 30 that are reduced in comparison to the proximal end 22 in the light-conducting device 20 or to the framing areas 33 and intervals 34 of the optical fibers 30. In addition, the described compression of the distal ends 38 of the optical fibers 30 can contribute to this effect. An additional reduction of the construction space taken up by the distal ends 38 of the optical fibers 30 and of the opening cross-sections on the distal end 18 of an endoscope 10 required for them, can be achieved by dispensing with the framing sheath 61.

Figure 5:
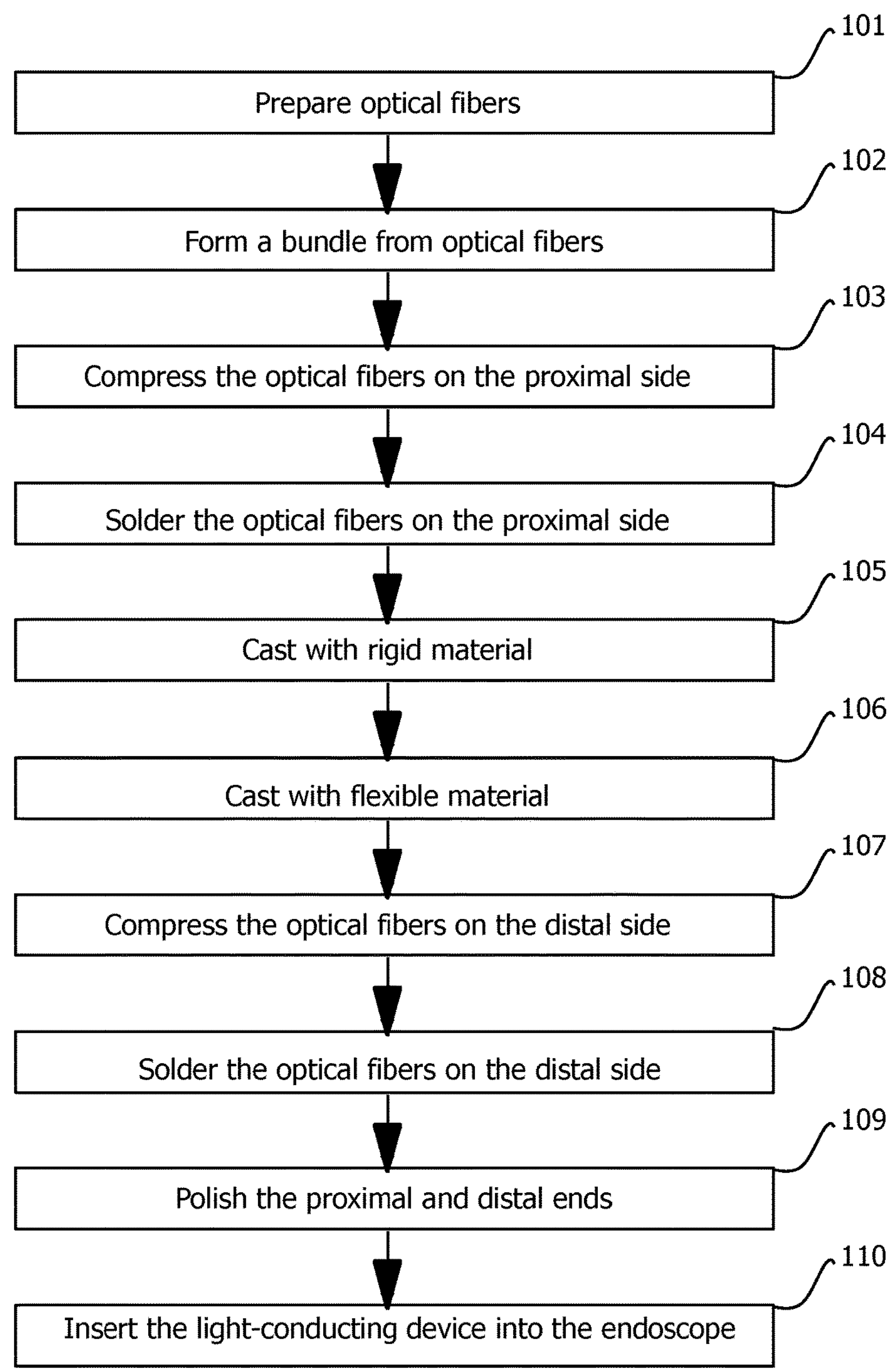
FIG. 5 shows a schematic flow diagram of a method to produce an endoscope.

FIG. 5 shows a schematic depiction of a method for producing an endoscope, in particular an endoscope as is described above with reference to FIG. 1. The first nine steps 101 through 109 constitute a method for producing a light-conducting device, in particular a light-conducting device as is described above with reference to FIGS. 2 through 4. The method for producing a light-conducting device can therefore be a part of a method for producing an endoscope. However, the method for producing a light-conducting device can be performed completely independently, in terms of space and time, of the tenth step 110 and logistically largely independently of the tenth step 110 and of the additional steps, not described here, in the framework of the production of an endoscope.

The method described schematically in FIG. 5 can be performed to produce a light-conducting device and an endoscope that both differ from those described above with reference to FIGS. 1 through 4. Hereinafter, for the sake of clarity, reference numbers from FIGS. 1 through 4 are used by way of example.

In a first step 101, a number of optical fibers 30 are prepared that each comprise a proximal end 32, a distal end 38, in a proximal area 33 a first cross-section 43 with a first surface area, and in a distal area 37 a second cross-section with a second surface area, such that the first surface area is larger or substantially larger than the second surface area.

In a second step 102, a bundle is formed from the number of optical fibers 30. Here the optical fibers 30 are combined, in particular, in their proximal areas 33, 34, 35 into a single bundle and in their distal area 37 into several separate bundles 371, 372.

In a third step 103, proximal areas 33 of the optical fibers 30 are insulated, in particular, by mechanical pressure in a plane perpendicular to the longitudinal axes of the optical fibers 30. The result of the insulation is, in particular, a hexagonal or essentially hexagonal arrangement of the proximal areas of the optical fibers 30. To reinforce the insulation, it is possible to provide a lubricating agent or a coating of the same that reduces the friction between the proximal areas 33 of the optical fibers 30.

In a fourth step 104, the proximal areas 33 of the optical fibers 30 are soldered together. For this purpose, the optical fibers are in particular heated to a temperature in the range of their glass transition or of their slumping temperature, such that mechanical pressure is simultaneously exerted.

In a fifth step 105, a first casting compound 55 is applied between transitional areas 35 of the optical fibers 30 in which the cross-sections of the optical fibers 30 are reduced downstream in the light path. The first casting compound 55 has, in particular, low elasticity. The elasticity of the first casting compound 55 is, in particular, adapted to the elasticity of the optical fibers 30 in their transitional areas 35 in order to mechanically reinforce the transitional areas 35 that can in some cases be very brittle and to reduce the risk of breakage.

In a sixth step 106, a second casting compound 56 is applied between the optical fibers 30 immediately distally from the area in which the first casting compound 55 is provided between the optical fibers 30. The second casting compound 56 has a higher or substantially higher elasticity than the first casting compound 55. The second casting compound 56 prevents or reduces the configuration of local maximums of mechanical tensions at the distal end of the rigid first casting compound 55.

In a seventh step 107, the distal ends 38 of the optical fibers 30 are compressed, in particular by mechanical pressure in a plane perpendicular to the longitudinal axes of the optical fibers 30. The result of the compression is, in particular, a hexagonal or essentially hexagonal arrangement of the distal areas of the optical fibers 30. To reinforce the compression, a lubricating agent or a coating of the same that reduces friction between the distal areas 38 of the optical fibers 30 can be provided.

In an eighth step 108, the distal ends 38 of the optical fibers 30 are soldered together. For this purpose, the optical fibers are heated, in particular, to a temperature in the range of their glass transition or of their slumping temperature, such that mechanical pressure is simultaneously exerted.

In a ninth step 109, the proximal ends 32 and/or the distal ends 38 of the optical fibers 30 are ground and, especially, polished in order to provide light inlet surfaces 31 or light outlet surfaces 39 of the individual optical fibers 30 and thus simultaneously a light inlet surface 21 and one or more light outlet surfaces 29 of the light-conducting device 20.

In a tenth step 110, the light-conducting device 20 produced in steps 101 through 109 is inserted in an endoscope body in order to form an endoscope 10. Because the light-conducting device 20 produced in steps 101 through 109 as described above has already largely or completely received all of its definitive characteristics outside the endoscope 10, no further processing steps are required on the light-conducting device 20 after insertion into the endoscope 10.

Contrary to the description presented above with reference to FIG. 5, a few steps can be executed in different sequences. In addition, steps can be omitted, for example the third step 103 for compression, the fifth step 105 and/or the sixth step 106 for casting and the ninth step for polishing, which can also be performed only after insertion of the light-conducting device 20 into the endoscope 10.

In addition, steps can be varied; for example, the optical fibers can be only cast or welded or cemented both proximally and distally as an alternative or in addition to soldering.

What is claimed is:

1. A light-conducting device for an endoscope to conduct illuminating light from a proximal end of the endoscope to a distal end of the endoscope, comprising:

a number of optical fibers, each optical fiber having a proximal end with a light inlet surface for positioning on the proximal end of the endoscope and a distal end with a light outlet surface for positioning on the distal end of the endoscope, each optical fiber having a first cross-section with a first surface area in a proximal region, a second cross-section with a second surface area in a distal region, and a third cross-section with a third surface area in a transitional area between the proximal region and the distal region, the first, second and third cross-sections are perpendicular to a longitudinal axis of the respective optical fiber, the first surface area is larger than the second surface area, and the third surface area constantly decreases downstream in a light path of the respective optical fiber from the proximal region to the distal region, a framing sheath, the proximal regions, the transitional areas and, at most, proximal portions of the distal regions of the number of optical fibers being positioned inside the framing sheath, the transitional area of each optical fiber being located between the proximal and distal regions and proximate to the proximal end of the respective optical fiber, a first casting compound surrounding the transitional areas and joining the optical fibers to the framing sheath to mechanically fix and stabilize the transitional areas relative to the framing sheath, the first casting compound being positioned between the transitional areas and joining the optical fibers to one another, and a second different casting compound positioned downstream in the light path from the first casting compound and between the optical fibers within the framing sheath, wherein the framing sheath has a coupling device to detachably fasten the framing sheath inside the proximal end of the endoscope at a coupling of the endoscope for optical and mechanical coupling with a light-conducting cable.

2. The light-conducting device according to claim 1, wherein the second casting compound has a higher elasticity than the first casting compound.

3. The light-conducting device according to claim 1, wherein the number of optical fibers are secured together in their proximal regions by soldering, melting, welding, cementing, or casting.

4. The light-conducting device according to claim 1, wherein at least some of the distal ends of the optical fibers of the number of optical fibers are secured together by soldering, melting, welding, cementing, or casting.

5. An endoscope comprising:

a light-conducting device, comprising a number of optical fibers, each optical fiber having a proximal end with a light inlet surface for positioning on a proximal end of the endoscope and a distal end with a light outlet surface for positioning on a distal end of the endoscope, each optical fiber having a first cross-section with a first surface area in a proximal region, a second cross-section with a second surface area in a distal region, and a third cross-section with a third surface area in a transitional area between the proximal region and the distal region, the first, second and third cross-sections are perpendicular to a longitudinal axis of the respective optical fiber, the first surface area is larger than the second surface area, and the third surface area constantly decreases downstream in a light path of the respective optical fiber from the proximal region to the distal region, a framing sheath, the proximal regions, the transitional areas and, at most, the proximal ends of the distal regions of the number of optical fibers being positioned inside the framing sheath, the transitional area of each optical fiber being located between the proximal and distal regions and proximate to the proximal end of the respective optical fiber, and a first casting compound surrounding the transitional areas and joining the optical fibers to the framing sheath to mechanically fix and stabilize the transitional areas relative to the framing sheath, the first casting compound being positioned between the transitional areas and joining the optical fibers to one another, and a second different casting compound positioned downstream in the light path from the first casting compound and between the optical fibers within the framing sheath, wherein the framing sheath has a coupling device to detachably fasten the framing sheath inside the proximal end of the endoscope at a coupling of the endoscope for optical and mechanical coupling with a light-conducting cable.

6. A method for producing an endoscope, having the following steps:

providing a light-conducting device comprising a number of optical fibers, each optical fiber having a proximal end with a light inlet surface for positioning on a proximal end of the endoscope and a distal end with a light outlet surface for positioning on a distal end of the endoscope, each optical fiber having a first cross-section with a first surface area in a proximal region, a second cross-section with a second surface area in a distal region, and a third cross-section with a third surface area in a transitional area between the proximal region and the distal region, the first, second and third cross-sections are perpendicular to a longitudinal axis of the respective optical fiber, the first surface area is larger than the second surface area, and the third surface area constantly decreases downstream in a light path of the respective optical fiber from the proximal region to the distal region, a framing sheath, the proximal regions, the transitional areas and, at most, proximal portions of the distal regions of the number of optical fibers being positioned inside the framing sheath, the transitional area of each optical fiber being located between the proximal and distal regions and proximate to the proximal end of the respective optical fiber, and a first casting compound surrounding the transitional areas and joining the optical fibers to the framing sheath to mechanically fix and stabilize the transitional areas relative to the framing sheath, the first casting compound being positioned between the transitional areas and joining the optical fibers to one another, and a second different casting compound positioned downstream in the light path from the first casting compound and between the optical fibers within the framing sheath, wherein the framing sheath has a coupling device to detachably fasten the framing sheath inside the proximal end of the endoscope at a coupling of the endoscope for optical and mechanical coupling with a light-conducting cable;

providing a subassembly for an endoscope; and inserting the light-conducting device into the subassembly in order to produce the endoscope.

7. The light-conducting device according to claim 1, wherein the proximal ends of the optical fibers are combined into a single bundle while the distal ends of the optical fibers are divided into a plurality of bundles that are positionable at different sites on the distal end of the endoscope.

8. The light-conducting device according to claim 1, wherein the distal regions of the optical fibers are longer than the proximal regions of the optical fibers.

9. The light-conducting device according to claim 1, wherein the framing sheath within the proximal end of the endoscope forms a part of the coupling of the endoscope.

10. The light-conducting device according to claim 1, wherein an elasticity of the first casting compound is adjusted to the elasticity of a material of the optical fibers to mechanically support the transitional areas of the optical fibers.

11. The light-conducting device according to claim 1, wherein the first casting compound is cement.

12. The light-conducting device according to claim 1, wherein the first casting compound is a thermoplastic or duroplastic synthetic material.

13. The light-conducting device according to claim 1, wherein the first casting compound is an organic material.

14. The light-conducting device according to claim 1, wherein the framing sheath has a shape of a cylindrical mantle with a circular, elliptical, or polygonal cross section.

* * * * *